(12) United States Patent
Pacelli et al.

(10) Patent No.: US 10,376,149 B2
(45) Date of Patent: Aug. 13, 2019

(54) ORAL CARE EVALUATION SYSTEM AND PROCESS

(71) Applicant: Colgate-Palmolive Company, New York, NY (US)

(72) Inventors: Michael Pacelli, West Caldwell, NJ (US); Hrebesh Molly Subhash, Highland Park, NJ (US); Michael Fitzgerald, Oakhurst, NJ (US); Harsh Mahendra Trivedi, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/646,257

(22) Filed: Jul. 11, 2017

(65) Prior Publication Data

US 2019/0014988 A1   Jan. 17, 2019

(51) Int. Cl.
*A61C 3/00* (2006.01)
*A61B 5/00* (2006.01)
*A61C 17/22* (2006.01)

(52) U.S. Cl.
CPC .......... *A61B 5/0088* (2013.01); *A61B 5/0071* (2013.01); *A61B 5/7445* (2013.01); *A61B 2576/00* (2013.01); *A61C 17/22* (2013.01)

(58) Field of Classification Search
CPC ................ A61B 5/0071; A61B 5/0088; A61B 2018/00982; A61B 1/043; A61B 5/0077; A61B 5/725; A61B 5/7264; A61B 5/7445; A61B 2576/00; A61C 19/063; A61C 17/22

USPC ....................................................... 250/458.1
See application file for complete search history.

(56) References Cited

U.S. PATENT DOCUMENTS

| | | | |
|---|---|---|---|
| 6,276,934 B1 | 8/2001 | Rakocz | |
| 7,057,639 B2 | 6/2006 | Spoonhower et al. | |
| 7,764,815 B2 | 7/2010 | Kim et al. | |
| 8,467,583 B2 | 6/2013 | Czerninski | |
| 8,839,476 B2 | 9/2014 | Adachi | |
| 9,566,225 B2 | 2/2017 | Sagel et al. | |
| 9,675,428 B2 | 6/2017 | Wu et al. | |
| 2003/0232303 A1* | 12/2003 | Black | A61N 5/0603 433/29 |
| 2004/0124366 A1* | 7/2004 | Zeng | A61B 5/448 250/458.1 |

(Continued)

OTHER PUBLICATIONS

Hitz Linden-Muller et al., 2015, "Diagnostics of tongue coating using autofluorescence," Swiss Dental Journal SSO 125:1674-1079.

(Continued)

*Primary Examiner* — Taeho Jo

(57) ABSTRACT

An oral care evaluation system may include: a light source configured to emit a spectrum of light which induces fluorescence in an organic compound, the light source illuminating soft oral tissue within an oral cavity; an image sensor receiving light generated by fluorescence of the organic compound on the soft oral tissue, the image sensor generating image data for an image of the oral tissue, the image comprising a plurality of pixels; and an image processor receiving the image data from the image sensor and programmed to evaluate oral hygiene of the soft oral tissue by assessing an attribute of each pixel in the image.

18 Claims, 6 Drawing Sheets

(56) References Cited

U.S. PATENT DOCUMENTS

| | | | |
|---|---|---|---|
| 2004/0248062 A1* | 12/2004 | Hahn | A61B 5/0088 433/89 |
| 2007/0239143 A1* | 10/2007 | Altshuler | A61B 18/203 606/9 |
| 2008/0060148 A1* | 3/2008 | Pinyayev | A61B 5/0088 15/22.1 |
| 2009/0076321 A1 | 3/2009 | Suyama et al. | |
| 2009/0132011 A1* | 5/2009 | Altshuler | A46B 15/0002 607/88 |
| 2009/0195385 A1* | 8/2009 | Huang | G08B 21/245 340/572.1 |
| 2010/0019170 A1* | 1/2010 | Hart | A61O 5/90 250/459.1 |
| 2010/0170052 A1* | 7/2010 | Ortins | A46B 15/0002 15/106 |
| 2011/0117025 A1* | 5/2011 | Dacosta | A61B 5/0059 424/9.6 |
| 2012/0061590 A1* | 3/2012 | Khojasteh | A61B 1/0638 250/459.1 |
| 2013/0203008 A1* | 8/2013 | Kressman | A46B 15/0034 433/27 |
| 2015/0164335 A1* | 6/2015 | Van Der Poel | A61C 9/0053 433/29 |
| 2015/0216398 A1* | 8/2015 | Yang | A61B 1/043 600/109 |
| 2015/0250572 A1* | 9/2015 | Gramann | A61B 1/0684 433/29 |
| 2015/0305624 A1 | 10/2015 | de Josselin de Jong | |
| 2016/0045114 A1* | 2/2016 | Dacosta | A61B 5/0059 600/476 |
| 2017/0116665 A1* | 4/2017 | Alzahrani | G06Q 30/0641 |
| 2017/0236281 A1* | 8/2017 | Dacosta | G06T 7/0016 382/128 |
| 2018/0080828 A1* | 3/2018 | Fink | G01J 3/508 |

OTHER PUBLICATIONS

Han et al., 2014, "Tongue images and tongue coating microbiome in patients with colorectal cancer," Microbial Pathogenesis 77:1-6.

International Search Report and Written Opinion of the International Searching Authority in International Application No. PCT/US2018/041263, dated Oct. 1, 2018.

Kim et al., 2014, "Tongue diagnosis system for quantitative assessment of tongue coating in patients with functional iyspepsia: A clinical trial," J. of Ethnopharmacology 155:709-713.

Lee et al., 2016, "Clinical Assessment of oral malodor using autofluorescence of tongue coating," Photodiagnosis and Photodynamic Therapy 13:323-329.

Panov et al., 2017, "Digital indexing the coated tongue," MedInform Issue 2, pp. 641-652.

Qi et al., 2016, "The classification of tongue colors with standardized acquisition and ICC profile correction in traditional Chinese medicine," BioMed Research International pp. 1-9.

Wang et al., 2013, "A high quality color imaging system for computerized tongue image analysis," Expert Systems with Applications 40:5854-5866.

Zhang et al., 2017, "Diagnostic method of diabetes based on support vector machine and tongue images," BioMed research International pp. 1-9.

Zhu et al., 2014, "A comparative study of contemporary color tongue image extraction methods based on HSI," International J. Of Biomedical Imaging pp. 1-10.

\* cited by examiner

ORAL CARE EVALUATION SYSTEM AND PROCESS

BACKGROUND

Dental professionals typically advise individuals to perform a regular brushing routine which includes brushing both the teeth and soft tissues within the oral cavity. It is widely recognized that bacteria on both teeth and soft tissues contributes to poor oral hygiene, which in turn can contribute to malodorous breath. Dental professionals have systems which are used to evaluate gingival plaque. Such systems must be used in the dental office and are generally not available for use at home. While systems and processes for evaluating the hygiene of soft tissues using other markers have been investigated, none exist which are convenient enough for use by dental professionals, let alone for home use. It is therefore desirable to have systems and processes which facilitate the evaluation of oral hygiene with respect to soft tissue, particularly the tongue, through the use of other markers that may be naturally present. Evaluations of this type can not only improve oral hygiene, and thus breath freshness, when used by dental professionals, but it can also be used at home for the same purposes.

BRIEF SUMMARY

Exemplary embodiments according to the present disclosure are directed to oral care evaluation systems and methods which are used to evaluate the amount of bacteria present on oral tissue such as the tongue. In one embodiment, the system illuminates oral tissue within the oral cavity using a wavelength which induces fluorescence in an organic compound and detects and analyzes the light resulting from the fluorescence in order to evaluate oral hygiene associated with the oral tissue.

In one aspect, the invention can be an oral care evaluation system including: a light source configured to emit a spectrum of light which induces fluorescence in an organic compound, the light source illuminating soft oral tissue within an oral cavity; an image sensor receiving light generated by fluorescence of the organic compound on the soft oral tissue, the image sensor generating image data for an image of the soft oral tissue, the image including a plurality of pixels; and an image processor receiving the image data from the image sensor and programmed to evaluate oral hygiene of the soft oral tissue by assessing an attribute of each pixel in the image.

In another aspect, the invention can be an oral care evaluation process including: illuminating soft oral tissue within an oral cavity with a light source emitting a spectrum of light which induces fluorescence in an organic compound; generating image data for an image of the soft oral tissue while illuminating the soft oral tissue, the image including a plurality of pixels; and evaluating oral hygiene using a programmable processor programmed to assess an attribute of each pixel of the image.

In still another aspect, the invention can be an oral care evaluation system including: an imaging subsystem including: a light source configured to emit a spectrum of light which induces fluorescence in an organic compound and to illuminate oral tissue within an oral cavity; and an image sensor positioned to receive light generated by fluorescence of the organic compound on the oral tissue and configured to generate image data for an image of the oral tissue, the image including a plurality of pixels; and an image processing subsystem configured to receive the image data from the image sensor and programmed to evaluate oral hygiene of the oral tissue by performing an assessment of an attribute of each pixel of the image, the assessment including: assigning one of a plurality of intensity values to each pixel; and counting a number of pixels associated with each of the plurality of intensity values.

In yet another aspect, the invention can be an oral care evaluation system including: a light source configured to emit a spectrum of light which induces fluorescence in an organic compound, the light source illuminating soft oral tissue within an oral cavity and the organic compound having a fluorescence spectrum; an image sensor receiving light in the fluorescence spectrum generated by fluorescence of the organic compound on the soft oral tissue, the image sensor generating image data for an image of the soft oral tissue, the image including a plurality of pixels; and an image processor receiving the image data from the image sensor and programmed to evaluate oral hygiene of the soft oral tissue by quantitative analysis to assess attributes of light in the fluorescence spectrum present in the image data.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The foregoing summary, as well as the following detailed description of the exemplary, embodiments, will be better understood when read in conjunction with the appended drawings. It should be understood, however, that the invention is not limited to the precise arrangements and instrumentalities shown in the following figures.

DETAILED DESCRIPTION

Figure 1:
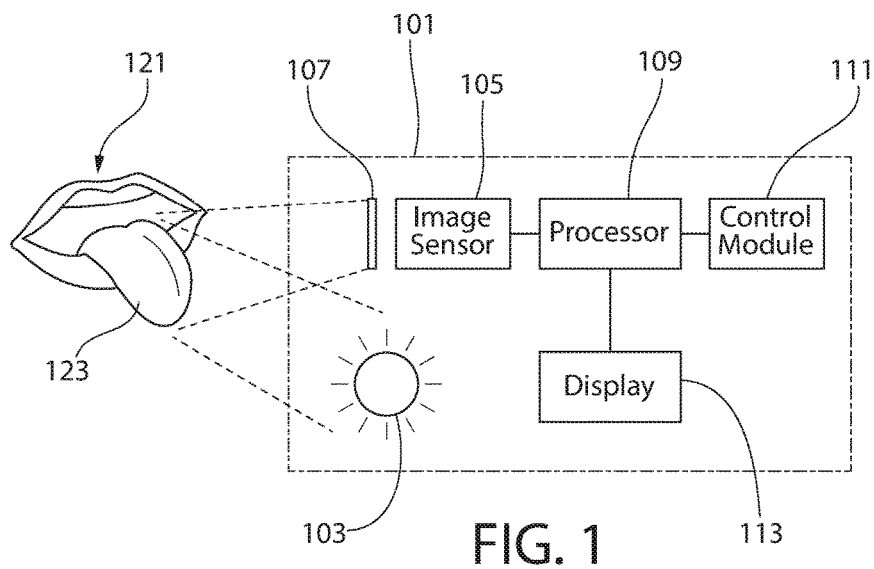
FIG. 1 schematically illustrates an oral care evaluation system in accordance with a first embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly, described otherwise. Moreover, the features and benefits of the invention are illustrated by reference to the preferred embodiments. Accordingly, the invention expressly should not be limited to such preferred embodiments illustrating some possible non-limiting combinations of features that may exist alone or in other combinations of features; the scope of the invention being defined by the claims appended hereto.

Features of the present invention may be implemented in software, hardware, firmware, or combinations thereof. The programmable processes described herein are not limited to any particular embodiment, and may be implemented in an operating system, application program, foreground or background processes, driver, or any combination thereof. The computer programmable processes may be executed on a single processor or on or across multiple processors.

Processors described herein may be any central processing unit (CPU), microprocessor, micro-controller, computational, or programmable device or circuit configured for executing computer program instructions (e.g. code). Various processors may be embodied in computer and/or server hardware and/or computing device of any suitable type (e.g. desktop, laptop, notebook, tablet, cellular phone, smart phone, PDA, etc.) and may include all the usual ancillary components necessary to form a functional data processing device including without limitation a bus, software and data storage such as volatile and non-volatile memory, input/output devices, a display screen, graphical user interfaces (GUIs), removable data storage, and wired and/or wireless communication interface devices including Wi-Fi, Bluetooth, LAN, etc.

Computer-executable instructions or programs (e.g. software or code) and data described herein may be programmed into and tangibly embodied in a non-transitory computer-readable medium that is accessible to and retrievable by a respective processor as described herein which configures and directs the processor to perform the desired functions and processes by executing the instructions encoded in the medium. A device embodying a programmable processor configured to such non-transitory computer-executable instructions or programs is referred to hereinafter as a "programmable device", or just a "device" for short, and multiple programmable devices in mutual communication is referred to as a "programmable system". It should be noted that non-transitory "computer-readable medium" as described herein may include, without limitation, any suitable volatile or non-volatile memory including random access memory (RAM) and various types thereof, read-only memory (ROM) and various types thereof, USB flash memory, and magnetic or optical data storage devices (e.g. internal/external hard disks, floppy discs, magnetic tape CD-ROM, DVD-ROM, optical disk, ZIP™ drive. Blu-ray disk, and others), which may be written to and/or read by a processor operably connected to the medium.

In certain embodiments, the present invention may be embodied in the form of computer-implemented processes and apparatuses such as processor-based data processing and communication systems or computer systems for practicing those processes. The present invention may also be embodied in the form of software or computer program code embodied in a non-transitory computer-readable storage medium, which when loaded into and executed by the data processing and communications systems or computer systems, the computer program code segments configure the processor to create specific logic circuits configured for implementing the processes.

Turning in detail to the drawings, FIG. 1 illustrates an oral care evaluation system 101 in accordance with an embodiment of the present invention. The oral care evaluation system 101 includes a light source 103 configured to emit a spectrum of light which induces fluorescence in an organic compound. The light source 103 may be any type of light source which is capable of emitting light in the desired spectrum, such as an LED or an incandescent light bulb. Other types of light sources may also be used, with the light source not limiting the scope of the invention unless otherwise expressly stated in the claims. The emission spectrum of the light source 103 is selected based upon the absorption spectrum of the targeted organic compound. In certain embodiments, the light source 103 may also include a light filter which limits the emission of light from the light source 103 to the desired emission spectrum.

In certain embodiments, the targeted organic compound is a porphyrin compound. In certain other embodiments, other fluorescing organic compounds may be targeted. Previous research has shown that many of the malodorous bacteria on oral tissue within the oral cavity, such as on the tongue, contain porphyrin compounds. Whereas the prior art uses subjective observations of fluorescence from porphyrin compounds in order to evaluate the hygiene of oral tissue, such as the tongue, the objective measures of fluorescence described herein provide better and more consistent evaluation results. To this end, the oral care evaluation system 101 is able to objectively evaluate the amount of the porphyrin compounds on oral tissues. And, because the porphyrin compounds are contained by bacteria, the objective evaluation of the porphyrin compounds may in turn be used as an objective evaluation of the amount of bacteria present on the oral tissue.

Porphyrin compounds are known to have an absorption spectrum with several absorption bands, with one band commonly referred to as the Soret band, and one or more other bands commonly referred to as the Q bands. The Soret band is used by the oral care evaluation system 101 to evaluate the amount of bacteria present on the tongue. The absorption spectrum of the Soret band is centered at a wavelength of about 400 nm and ranges in wavelength from about 350 nm to 450 nm. Thus, the light source 103 is selected and/or configured to emit a spectrum of light having wavelengths of between 350 nm to 450 nm. In certain embodiments, the light source 103 may emit a narrower spectrum, so long as the emitted spectrum still has an effective overlap with the absorption spectrum of the organic compound. In still other embodiments, the spectrum of light emitted from the light source 103 may include wavelengths less than 350 nm, and/or it may include wavelengths over 450 nm. In certain other embodiments, a VELscope® Vx device, manufactured by LED Medical Diagnostics Inc. of Atlanta, Ga., may be used as the light source 103. The VELscope® Vx device is commonly used to detect soft tissue abnormalities, and it emits light in the spectral range of about 400 nm to 460 nm.

Porphyrin compounds are also known to have a fluorescence spectrum ranging in wavelength from about 625 nm to about 750 nm. The image sensor 105 is therefore positioned and configured to detect light in this spectral range. As should be appreciated, oral tissue with more bacteria generates more fluorescent light in this spectral range. In certain other embodiments in Which other organic compounds are induced to fluoresce, the image sensor 105 is configured to detect light in the fluorescence spectrum of the targeted organic compound.

The image sensor 105 generates image data for an image of the oral tissue while the oral tissue is being illuminated by light emitted from the light source 103, i.e., while the organic compound is fluorescing. A light filter 107 is included as part of the oral care evaluation system 101 to filter light incident on the image sensor 105, with the purpose being to limit the incident light to the fluorescence spectrum of the porphyrin compound. In certain embodiments, the light filter 107 may be omitted where the image sensor 105 has limited or no sensitivity to light outside of the fluorescence spectrum of the organic compound. In other embodiments, the image sensor 105 may be a broad spectrum image sensor, with data relating to the fluorescence spectrum of the organic compound being determined and analyzed through subsequent image processing.

In certain embodiments, the image sensor 105 may be a charge-coupled device (CCD). In certain other embodiments, the image sensor 105 may be a digital camera (which itself may include a MD). In such embodiments, the flash of the digital camera may be configured to serve as the light source 103 for the oral care evaluation system 101. Other types of image sensors may also be used, with the image sensor not limiting the scope of the invention unless otherwise expressly, stated in the claims.

The image processor 109 is a programmable processor which is communicably coupled to the image sensor 105 so that the image data for the image of the oral tissue may be transmitted from the image sensor 105 and received by the image processor 109. In certain embodiments, the image sensor 105 and the image processor 109 may be communicably coupled through a wired connection. The communication connection between the image sensor 105 and the image processor 109 allows the image sensor 105 to send image data to the image processor 109, and it allows the image processor 109 to send command signals to control operation of the image sensor 105. In alternative embodiments, the image processor 109 and the image sensor 105 may communicate using a wireless connection. In such embodiments, the wireless connection may use any type of appropriate wireless protocol for communications, such as, for example, Bluetooth®, WiFi, cellular, and the like.

The image processor 109 is also communicably coupled to a control module 111 and to the light source 103. Through the communication connection between the image processor 109 and the light source 103, the image processor is able to control operation of the light source 103, such as for turning the light source 103 on and off. The control module 111 serves as a user interface for the system 101, allowing the user to turn the light source 103 on and off, to control when the image sensor 105 is operational to generate image data for the oral tissue, and to otherwise interact with the image processor 109. The control module 111 may take any different form, such as one or more buttons or switches, a keypad or keyboard, or even a touch screen. Other types of control modules may also be used, with the control module not limiting the scope of the invention unless otherwise expressly stated in the claims. In certain embodiments, the control module may also provide feedback to the user about the oral hygiene evaluation being performed.

The image processor 109 is also communicably coupled to a display 113, through which the image processor 109 is able to display an image of the oral tissue and/or results of the oral hygiene evaluation. In certain embodiments, the results of the oral hygiene evaluation may be a hygiene grade. The communication connections between the image processor 109, on the one hand, and any one or more of the light source 103, the control module 111, and the display 113 may be through a wired connection or through a wireless connection.

As is described in greater detail below, during operation of the oral care evaluation system 101, the light source 103 emits a spectrum of light which induces fluorescence in an organic compound, with the light illuminating oral tissue, such as the tongue 123, within the oral cavity 121. The image sensor 105 detects light from the fluorescing organic compound and generates image data for an image of the oral tissue. The image processor 109 is programmed to assess an attribute of each pixel in the image in order to evaluate the oral hygiene associated with the oral tissue. The image processor 109 is further programmed to communicate the evaluation to a user, such as by displaying the image of the oral tissue and/or the hygiene grade on a display screen.

Figure 2:
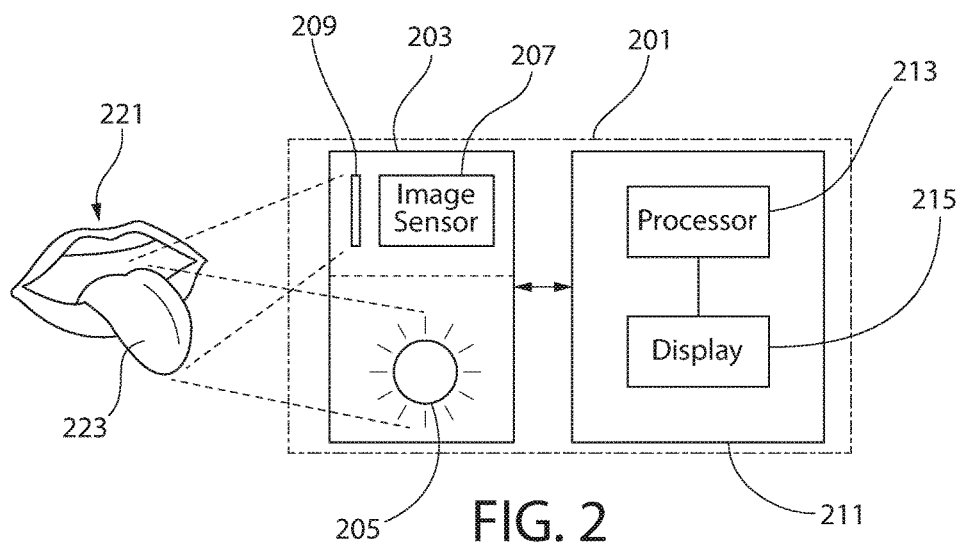
FIG. 2 schematically illustrates an oral care evaluation system in accordance with a second embodiment of the present invention.

FIG. 2 illustrates an oral care evaluation system 201 in accordance with another embodiment of the present invention. The oral care evaluation system 201 includes an imaging subsystem 203 and an image processing subsystem 211. The imaging subsystem 203 includes a light source 205, an image sensor 207, and a light filter 209. The light source 205 may be any type of light source which is capable of emitting light in the desired spectrum, such as an LED or an incandescent light bulb. Other types of light sources may also be used, with the light source not limiting the scope of the invention unless otherwise expressly stated in the claims. As previously described, the emission spectrum of the light source 205 is selected based upon the absorption spectrum of the targeted organic compound, and the targeted organic compound, in certain embodiments, may be a porphyrin compound. In certain embodiments, the light source 205 is selected and/or configured to emit a spectrum of light having wavelength of between 350 nm to 450 nm. In certain other embodiments, the light source 205 may emit a narrower spectrum, so long as the emitted spectrum still has an effective overlap with the absorption spectrum of the targeted organic compound. In still other embodiments, the spectrum of light emitted from the light source 205 may include wavelengths less than 350 nm, and/or it may include wavelengths over 450 nm. In certain embodiments, the light source 205 may also include a light filter which limits the emission of light from the light source 205 to the desired emission spectrum.

The image sensor 207 is configured to detect light in the spectral range of light emitted from the fluorescing organic compound. The light filter 209 is included to filter light incident on the image sensor 207, with the purpose being to limit the incident light to the fluorescence spectrum of the porphyrin compound. In certain embodiments, the light filter 209 may be omitted where the image sensor 207 has limited or no sensitivity to light outside of the fluorescence spectrum of the organic compound. The image sensor 207 generates image data for an image of the oral tissue while the organic compound is fluorescing. In certain embodiments, the image sensor 207 may be a CCD. Other types of image sensors may also be used, with the image sensor not limiting the scope of the invention unless otherwise expressly stated in the claims.

The image processing subsystem 211 is communicably coupled to the imaging subsystem 203 so that image data for the image of the oral tissue may be transmitted from the imaging subsystem 203 and received by the image processing subsystem 211. In certain embodiments, the imaging subsystem 203 and the image processing subsystem 211 may be communicably coupled through a wired connection. The communication connection between the imaging subsystem 203 and the image processing subsystem 211 also allows the image processing subsystem 211 to send command signals to control operation of the imaging subsystem 203. In alternative embodiments, the image processing subsystem 211 and the imaging subsystem 203 may communicate using a wireless connection. In such embodiments, the wireless connection may use any type of appropriate wireless protocol for communications, such as, for example, Bluetooth®, WiFi, cellular, and the like.

The image processing subsystem 211 includes a programmable processor 213 and a display screen 215 communicably coupled to each other. The programmable processor 213 is programmed to control the light source 205 and the image sensor 207, such that during operation of the oral care evaluation system 201, the light source 205 emits a spectrum of light which induces fluorescence in an organic compound, with the light illuminating oral tissue, such as the tongue 223, within the oral cavity 221. By controlling the light source 205 and the image sensor 207 in this manner, the programmable processor 213 is able to obtain image data while the organic compound is fluorescing. The programmable processor 213 is also programmed to control the display screen 215 so that the image of the oral tissue and/or a hygiene grade may be displayed to the user. IN certain embodiments, the programmed functionality of the programmable processor 213 may be as described below in connection with the process for evaluating oral hygiene. In certain embodiments, the display screen 215 may be a touch sensitive screen which accepts input from a user in response to touches on the touch sensitive screen. In such embodiments, the programmable processor 213 may control the light source 205 and the image sensor 207 in response to input received from the user through the display screen 215.

In certain embodiments, the image processing subsystem 211 may also include a volatile and/or non-volatile memory, which may be used for storing programming and for storing data. In such embodiments, the memory may also be used to store historical data. In certain embodiments, the image processing subsystem 211 may be a computing device such as, for example, a laptop, a smart phone, a tablet, a PDA, and the like. In still other embodiments, the image processing subsystem 211 may also communicate with a server (not shown) for purposes of storing historical data and/or to provide server-side processing functionality.

Figure 3:
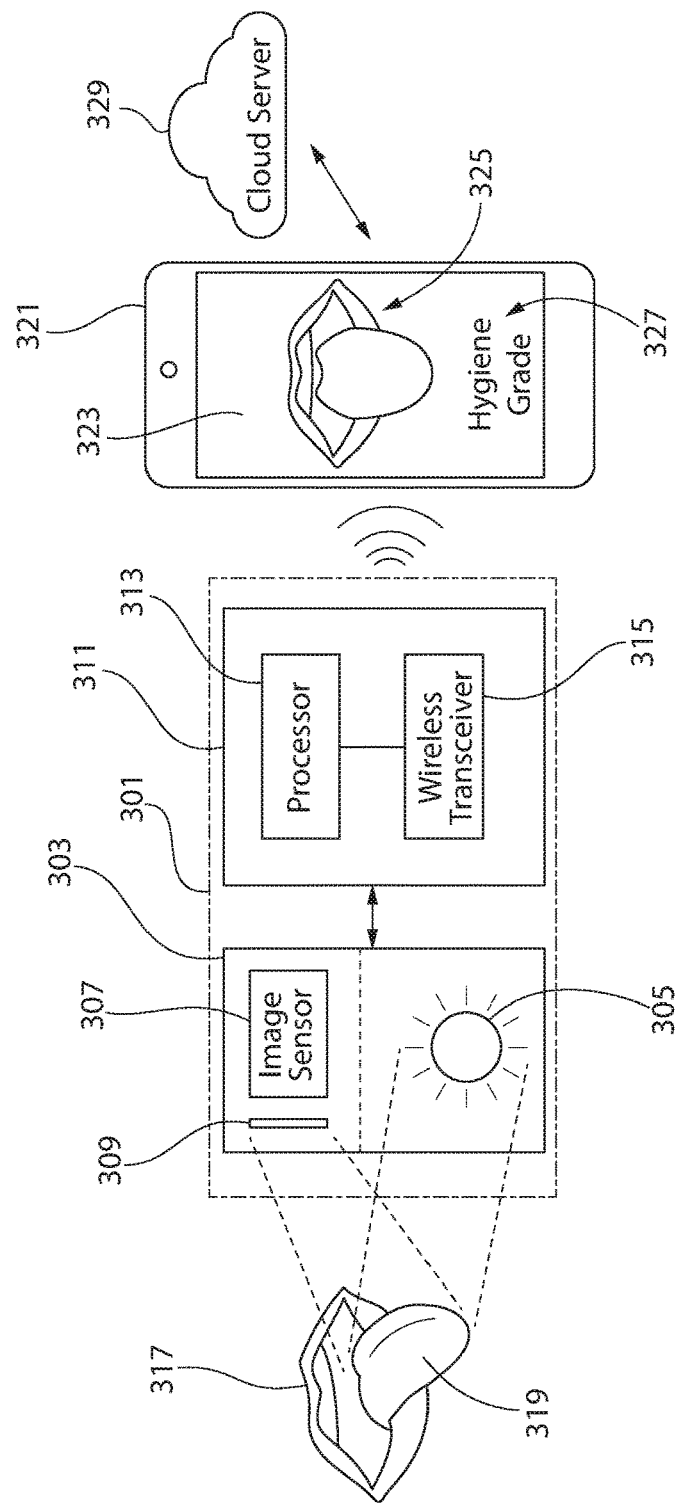
FIG. 3 schematically illustrates an oral care evaluation system in accordance with a third embodiment of the present invention.

FIG. 3 illustrates an oral care evaluation system 301 in accordance with another embodiment of the present invention. The oral care evaluation system 301 includes an imaging subsystem 303 and an image processing subsystem 311. The imaging subsystem 303 includes a light source 305, an image sensor 307, and a light filter 309. The light source 305 may be any type of light source which is capable of emitting light in the desired spectrum, such as an LED or an incandescent light bulb. Other types of light sources may also be used, with the light source not limiting the scope of the invention unless otherwise expressly stated in the claims.

As previously described, the emission spectrum of the light source 305 is selected based upon the absorption spectrum of the targeted organic compound, and the targeted organic compound, in certain embodiments, may be a porphyrin compound. In certain embodiments, the light source 305 is selected and/or configured to emit a spectrum of light having wavelength of between 350 nm to 450 nm. In certain other embodiments, the light source 305 may emit a narrower spectrum, so long as the emitted spectrum still has an effective overlap with the absorption spectrum of the targeted organic compound. In still other embodiments, the spectrum of light emitted from the light source 305 may include wavelengths less than 350 nm, and/or it may include wavelengths over 450 nm. In certain embodiments, the light source 305 may also include a light filter which limits the emission of light from the light source 305 to the desired emission spectrum.

The image sensor 307 is configured to detect light in the spectral range of light emitted from the fluorescing organic compound. The light filter 309 is included to filter light incident on the image sensor 307, with the purpose being to limit the incident light to the fluorescence spectrum of the porphyrin compound. In certain embodiments, the light filter 309 may be omitted where the image sensor 307 has limited or no sensitivity to light outside of the fluorescence spectrum of the organic compound. The image sensor 307 generates image data for an image of the oral tissue while the organic compound is fluorescing. In certain embodiments, the image sensor 307 may be a CCD. Other types of image sensors may also be used, with the image sensor not limiting the scope of the invention unless otherwise expressly stated in the claims.

The image processing subsystem 311 is communicably coupled to the imaging subsystem 303 so that image data for the image of the oral tissue may be transmitted from the imaging subsystem 303 and received by the image processing subsystem 311. The communication connection between the imaging subsystem 303 and the image processing subsystem 311 also allows the image processing subsystem 311 to send command signals to control operation of the imaging subsystem 303. In this embodiment, the imaging subsystem 303 and the image processing subsystem 311 are communicably coupled through a wired connection.

The image processing subsystem 311 includes a programmable processor 313 and a wireless transceiver 315 which are communicably coupled to each other. In certain embodiments, the image processing subsystem 311 may also include a volatile and/or non-volatile memory, which may be used for storing programming and/or data. The wireless transceiver 315 may be configured to transmit the image data using any type of appropriate wireless protocol for communications. Non-limiting examples of wireless protocols include Bluetooth®, WiFi, cellular, and the like. The programmable processor 313 is programmed to control the light source 305 and the image sensor 307, such that during operation of the oral care evaluation system 301, the light source 305 emits a spectrum of light which induces fluorescence in an organic compound, with the light illuminating oral tissue, such as the tongue 319, within the oral cavity 317. By controlling the light source 305 and the image sensor 307 in this manner, the programmable processor 313 is able to generate image data while the organic compound is fluorescing. The programmed functionality of the programmable processor 313 for generating the image data is described in greater detail below.

Evaluation of the generated image data may be performed by the programmable processor 313, by the remote device 321, or by a combination of the programmable processor 313 and the remote device 321. The remote device 321 is a general computing device such as, for example, a laptop, a smart phone, a tablet, a PDA, and the like. In certain embodiments, the remote device 321 may be programmed with functionality to fully evaluate the image data as described herein. The remote device 321 is also programmed to display the evaluation results on the display screen 323. In certain embodiments, the evaluation results displayed on the display screen 323 may be the image of the oral cavity 325, which includes the oral tissue being evaluated, and/or the hygiene grade 327.

In certain embodiments, the remote device 321 may also be used to control the functionality of the programmable processor 313. In such embodiments, the remote device 321 may accept input from a user and send control commands to the programmable processor 313 in response to the user input.

The remote device 321 may also communicate with a cloud server 329 using one or more public or private local area networks (LAN) and/or wide area networks (WAN). In certain embodiments, the remote device 321 may communicate one or more of the image data, the evaluation results, and any meta data associated with the evaluation with the cloud server 329. In certain embodiments, the cloud server 329 may be used to store historical data associated with oral care evaluations. In still other embodiments, the cloud server 329 may be used as a data aggregator, and the cloud server 329 may be used to perform additional data analysis, both on individual evaluations and on aggregated evaluations.

Figures 4A, 4B:
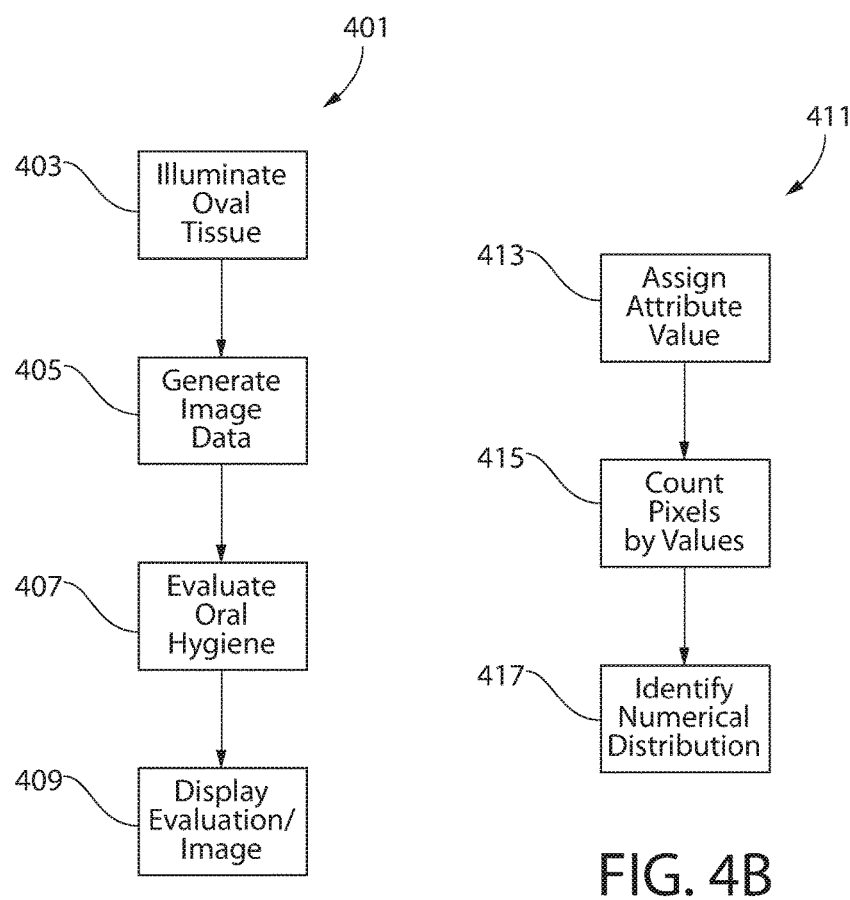
FIG. 4A is a flowchart showing a process for evaluating oral hygiene.
FIG. 4B is a flowchart showing an image assessment process.

FIGS. 4A-B are flowcharts 401, 411 showing a process for evaluating oral hygiene. The programmable processors described above in connection with embodiments of the invention may be programmed to follow the process of the flowcharts 401, 411. In addition, the capabilities and parameters of the embodiments described above may be incorporated into the process of the flowcharts 401, 411. In certain embodiments, the processes shown and described herein may performed by a plurality of processors, with each processor being programmed to perform only a portion of the process, and with all the processors together being programmed to perform the entirety of the process.

As shown in FIG. 4A, the process begins with a step of illuminating 403 oral tissue within an oral cavity with a light source emitting a spectrum of light which induces fluorescence in an organic compound. In certain embodiments, the light source may be any type of light source which emits light in a spectrum, as described above, which induces fluorescence in an organic compound. In certain embodiments, the targeted organic compound is a porphyrin compound, and the light spectrum emitted by the light source overlaps, at least partially, with the absorption spectrum of the porphyrin compound.

While the organic compound is fluorescing, the process continues with a step of generating image data 405 for an image of the oral tissue. In certain embodiments, the image data may be generated by an image sensor receiving light from the fluorescing porphyrin compound. The image of the oral tissue is a digital image, and as such the digital image includes a plurality of pixels. In certain embodiments, the digital image has a pixel resolution of at least 640×480. In certain other embodiments, the digital image may have a pixel resolution of less than 640×480, such as 320×240 or even less. It should be understood that the tradeoff for using a digital image with a lower pixel resolution is that the accuracy of the evaluation may decrease as the pixel resolution decreases. In certain embodiments, each pixel may be independently defined within the image data. In certain other embodiments, such as for image data that represents a compressed image, each pixel is independently defined only after the compressed image data is decompressed. In certain embodiments, the image data may conform to a standardized image format, such as gif, jpg, tif, png, and the like.

In the next step, the process continues with evaluating 407 oral hygiene. In certain embodiments, the results of the evaluation may be in the form of a hygiene grade, which is an assigned value used to inform the user about the results of the oral hygiene evaluation. In such embodiments the assigned value is a hygiene grade, which may be a numeric score ranging from 1-5, or 1-10, or it may be an alphabetical score ranging from A-F. Once the evaluation 407 is completed, the image and/or the results of the evaluation, such as the hygiene grade, are displayed 409 on a display screen.

FIG. 4B is a flowchart 411 which illustrates details of the evaluation 407 step in FIG. 4A. As a first step during the evaluation 407, an attribute of each pixel of the image is assessed and an attribute value is assigned 413 to each pixel. In certain embodiments, the attribute assessed is the intensity of each pixel. In still other embodiments, other attributes of each pixel may be assessed in addition to or instead of the intensity. The assigned attribute value is based on the assessed attribute of each individual pixel and the overall range of the assessed attributes amongst all pixels. The assigned attribute values have a predetermined range, such as from 0-255, with 0 representing a lower intensity than 255. The number of attribute values within the range may vary, however, the range should include a sufficient number of attribute values to create a meaningful distribution for the assessed attribute. Once the attribute values are assigned 413, then in the next step the number of pixels associated with each attribute value are counted 415. Once all the attribute values are counted, the evaluation process ends with identifying 417 the numerical distribution of the counted and assigned attribute values.

Figure 5:
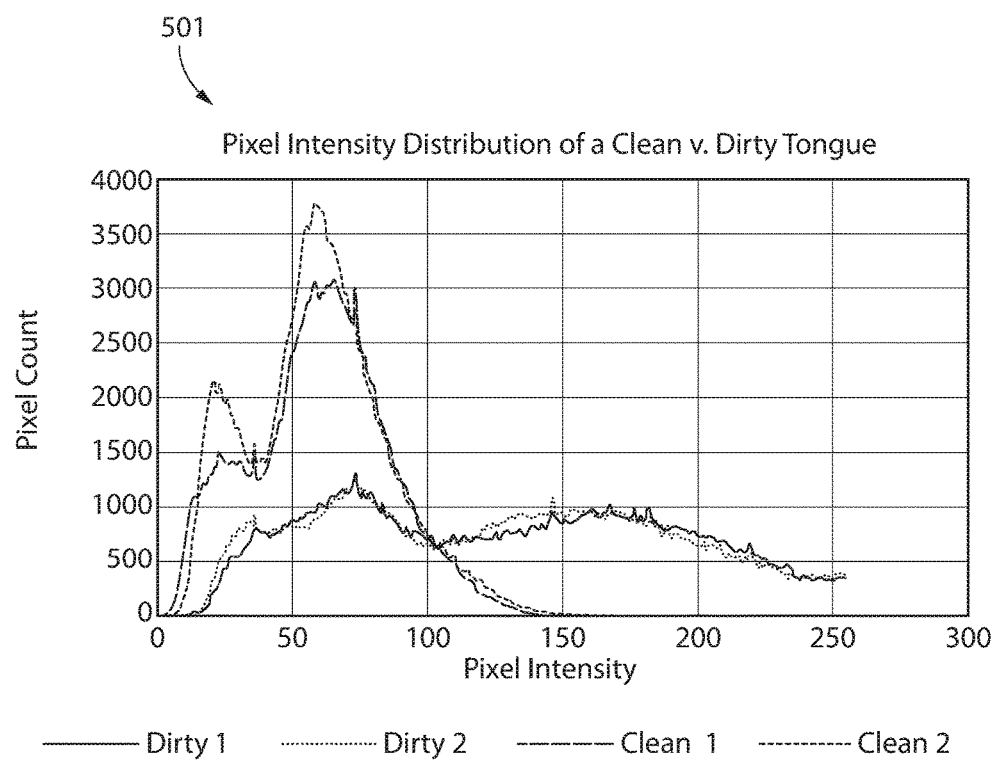
FIG. 5 illustrates a graph illustrating sample data comparing a plurality of image assessments.

FIG. 5 is a graph 501 which shows four different sample numerical distributions for assessed intensity based on fluorescing images generated from tongues. The x-axis of the graph 501 represents the range of attribute values that are assigned to the pixels based on the assessed intensity, and the y-axis represents the number of pixels counted as a function of the attribute value. In the graph 501, dirty tongues 1 and 2 have a larger number of pixels in the higher intensity region above the attribute value of 150, and therefore a corresponding lower number of pixels in the lower intensity region below the attribute value of 150. Also, for 501 tongues 1 and 2, nearly all pixels are assigned an attribute value below 150. Thus, the graph 501 illustrates that a distinct difference exists between the attribute value distribution for a dirty tongue as compared to the attribute value distribution for a clean tongue when the attribute is the intensity of the pixels. From these differences, and because the intensity value distribution correlates with the amount of bacteria present on the tongue, a hygiene grade may be generated for each of the numerical distributions. For example, on a scale of 1-5, a 1 on this hygiene scale may represent an image having more than a nominal number of pixels counted for intensity values over 200, such as is seen for the dirty tongues 1 and 2. Also, a 5 on this hygiene scale may represent an image having any intensity value between 0-100 which also has a pixel count for any intensity value above 2500, such as is seen for the clean tongues 3 and 4.

Figure 6:
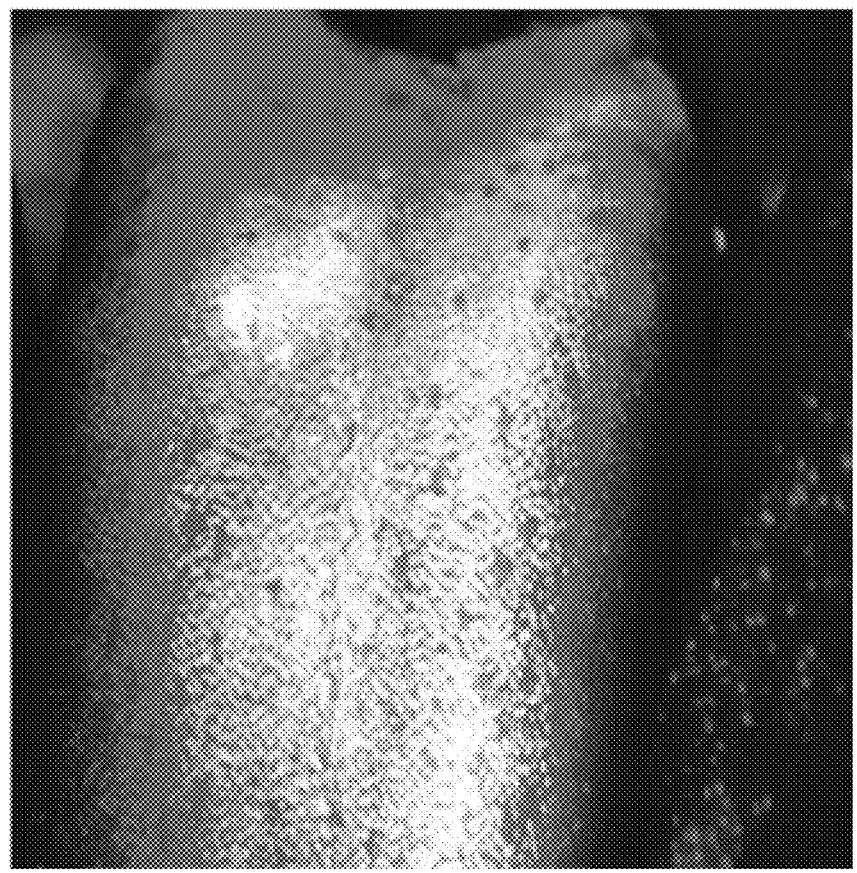
FIG. 6 is a grayscale image of a tongue before being cleaned.
Figure 7:
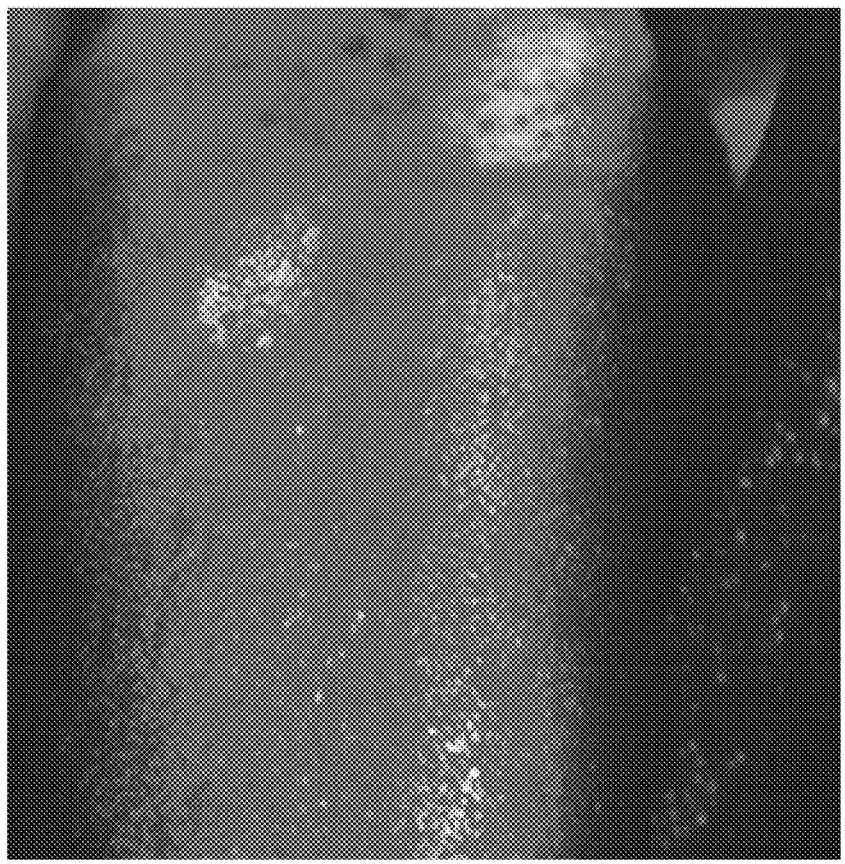
FIG. 7 is a grayscale image of a tongue after being cleaned.

Two images are presented to illustrate the differences seen in the intensity distributions in the graph of FIG. 5; FIG. 6 is an image showing a tongue before cleaning, and FIG. 7 is an image showing a tongue after cleaning. As can be seen by comparison of these two images; the image of FIG. 6 has a greater number of high intensity pixels as compared to the image of FIG. 7. These differences are reflected in the differences in the dirty tongues versus the clean tongues in the graph 501 of FIG. 5.

As used throughout; ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral care evaluation system comprising:
a light source configured to emit a spectrum of light which induces fluorescence in an organic compound, the light source illuminating soft oral tissue within an oral cavity;
an image sensor receiving light generated by fluorescence of the organic compound on the soft oral tissue, the image sensor generating image data for an image of the soft oral tissue, the image comprising a plurality of pixels; and
an image processor receiving the image data from the image sensor and programmed to evaluate oral hygiene of the soft oral tissue by assessing an attribute of each pixel in the image;
wherein the image processor is programmed to display a hygiene grade on the display screen, the hygiene grade resulting from the evaluation of oral hygiene.

2. The system of claim 1, wherein the soft oral tissue comprises a tongue.

3. The system of claim 1, wherein the attribute comprises intensity.

4. The system of claim 1, wherein the organic compound comprises a porphyrin compound.

5. The system of claim 1, wherein the spectrum of light comprises light having a wavelength in the range of 400 nm to 460 nm.

6. The system of claim 1, further comprising a light filter positioned to limit light received by the image sensor to a predetermined spectrum of light.

7. The system of claim 6, wherein the predetermined spectrum comprises the spectrum of fluorescence of a porphyrin compound.

8. The system of claim 1, wherein while assessing the attributes of the pixels, the image processor is programmed to assign one of a plurality of attribute values to each pixel and to count a number of pixels associated with each of the plurality of attribute values.

9. The system of claim 8, wherein the image processor is further programmed to evaluate oral hygiene based upon a numerical distribution of counted pixels versus the attribute values.

10. The system of claim 1, further comprising a display screen communicably coupled to the image processor, wherein the image processor is programmed to display the image of the soft oral tissue on the display screen.

11. An oral care evaluation system comprising:
an imaging subsystem comprising:
a light source configured to emit a spectrum of light which induces fluorescence in an organic compound and to illuminate oral tissue within an oral cavity; and
an image sensor positioned to receive light generated by fluorescence of the organic compound on the oral tissue and configured to generate image data for an image of the oral tissue, the image comprising a plurality of pixels; and
an image processing subsystem configured to receive the image data from the image sensor and programmed to evaluate oral hygiene of the oral tissue by performing an assessment of an attribute of each pixel of the image, the assessment comprising:
assigning one of a plurality of attribute values to each pixel; and
counting a number of pixels associated with each of the plurality of attribute values;
wherein the image processing subsystem is further programmed to evaluate oral hygiene based upon a numerical distribution of counted pixels versus the intensity values.

12. The system of claim 11, wherein the oral tissue comprises a tongue.

13. The system of claim 11, wherein the attribute comprises intensity.

14. The system of claim 11, wherein the organic compound comprises a porphyrin compound.

15. The system of claim 11, wherein the spectrum of light comprises light having a wavelength in the range of 400 nm to 460 nm.

16. The system of claim 11, wherein the imaging subsystem further comprises a light filter positioned to limit light received by the image sensor to a predetermined spectrum of light, and wherein the predetermined spectrum comprises the spectrum of fluorescence of a porphyrin compound.

17. The system of claim 11, further comprising a display screen communicably coupled to the image processing subsystem, wherein the image processing subsystem is programmed to display the image of the oral tissue on the display screen, and wherein the image processing subsystem is programmed to display a hygiene grade on the display screen, the hygiene grade resulting from the evaluation of oral hygiene.

18. An oral care evaluation system comprising:
a light source configured to emit a spectrum of light which induces fluorescence in an organic compound, the light source illuminating soft oral tissue within an oral cavity and the organic compound having a fluorescence spectrum;
an image sensor receiving light in the fluorescence spectrum generated by fluorescence of the organic compound on the soft oral tissue, the image sensor generating image data for an image of the soft oral tissue, the image comprising a plurality of pixels;
an image processor receiving the image data from the image sensor and programmed to evaluate oral hygiene of the soft oral tissue by quantitative analysis to assess attributes of light in the fluorescence spectrum present in the image data; and a display providing the user with a hygiene grade indicating the state of the user's breath.

\* \* \* \* \*